United States Patent [19]

Boger

[11] Patent Number: 5,104,877
[45] Date of Patent: Apr. 14, 1992

[54] PSORIASIS TREATMENT

[75] Inventor: Robert S. Boger, Lake Forest, Ill.

[73] Assignee: Abbott Laboratories, Abbott Park, Ill.

[21] Appl. No.: 661,563

[22] Filed: Feb. 25, 1991

[51] Int. Cl.$^5$ ............................................ A61K 31/505
[52] U.S. Cl. .................................... 514/256; 514/242;
514/252; 514/255; 514/269; 514/275; 514/340;
514/863
[58] Field of Search ............... 514/256, 242, 252, 255, 514/269, 275, 340, 863

[56] References Cited

U.S. PATENT DOCUMENTS

| | | | |
|---|---|---|---|
| 4,355,040 | 10/1982 | Furukawa et al. | 514/600 |
| 4,816,463 | 3/1989 | Blankley et al. | 514/293 |
| 4,880,804 | 11/1989 | Carini et al. | 514/234.5 |

OTHER PUBLICATIONS

Ena, et al., Acta Cardiologica XL 199 (1985).
Ryder, et al., Clin. Chem. Acta 153 143 (1985).
Powell, et al., Science 245 186 (1989).

*Primary Examiner*—Leonard Schenkman
*Attorney, Agent, or Firm*—Steven R. Crowley

[57] ABSTRACT

The present invention relates to the use of angiotensin II antagonists for the treatment of psoriasis.

5 Claims, No Drawings

PSORIASIS TREATMENT

TECHNICAL FIELD

The present invention relates to the use of angiotensin II antagonists for the treatment of psoriasis.

BACKGROUND ART

Psoriasis is a chronic skin disease which is known to be difficult to treat. Psoriasis is characterized by discrete and confluent, reddish, silvery-scaled maculopapules. These psoriatic lesions occur most often on the elbows, knees, trunk and scalp. Current treatments for psoriasis include the use of agents such an anthralin (dihydroxyanthralin), azarabine, colchicine, fluorouracil, methotrexate, methoxsalen (8-methoxypsoralen), resorcinol, retinoids (for example, retinoic acid), corticosteroids (for example, clobetasol propionate, triamcinolone acetonide and the like), cyclosporin, iodochlorhydroxyquin, salicylic acid, vitamin D, dapsone, somatostatin, sulfur, tars and zinc oxide. Ultra-violet light treatment, alone or in combination with other agents such as psoralen (i.e., PUVA therapy), is also used to treat psoriasis.

There are reports that the activity of the renin-angiotensin-aldosterone system is enhanced in patients with psoriasis (Ena, et al., Acta Cardiologica XL 199 (1985); Ryder, et al., Clin. Chem. Acta 153 143 (1985)). However, there is no established cause and effect relationship between the renin-angiotensin-aldosterone system and psoriasis.

The enzyme renin cleaves the circulating peptide angiotensinogen to produce angiotensin I (AI). Angiotensin converting enzyme (ACE) then cleaves angiotensin I to produce angiotensin II. Angiotensin II causes vasoconstriction and stimulation of the adrenal cortex to release aldosterone, a hormone which causes sodium retention. Sodium retention causes blood volume to increase, which leads to hypertension.

Angiotensin II antagonists have been disclosed as agents for the treatment of hypertension, congestive heart failure, renal failure and elevated intraocular pressure.

DISCLOSURE OF THE INVENTION

It has now been found that angiotensin II antagonists are useful for the treatment of psoriasis.

Examples of angiotensin II antagonists and methods for their preparation include, but are not limited to, those disclosed in the following references:

1. Carini, et al., U.S. Pat. No. 4,880,804, issued Nov. 14, 1989, which is hereby incorporated by reference;
2. Furukawa, et al., U.S. Pat. No. 4,355,040, issued Oct. 19, 1982, which is hereby incorporated by reference;
3. Furukawa, et al., U.S. Pat. No. 4,582,847, issued Apr. 15, 1986, which is hereby incorporated by reference;
4. Blankley, et al., U.S. Pat. No. 4,812,462, issued Mar. 14, 1989, which is hereby incorporated by reference;
5. Blankley, et al., U.S. Pat. No. 4,816,463, issued Mar. 28, 1989, which is hereby incorporated by reference;
6. Carini, et al., European Patent Application No. EP324377, published July 19, 1989;
7. Carini, et al., European Patent Application No. EP323841, published July 12, 1989;
8. Carini, et al., European Patent Application No. EP253310, published Jan. 20, 1988 (including, 2-butyl-4-chloro-1-((2'-(1H-tetrazol-5-yl)biphenyl-4-yl)methyl)-5-(hydroxylmethyl)imidazole or 2-butyl-4-chloro-1-((2'-(1H-tetrazoly-5-yl)biphenyl-4-yl)methyl)-5-(carboxy)imidazole);
9. Ardecky, et al., PCT Patent Application No. WO91/00277, published Jan. 10, 1991;
10. Ardecky, et al., PCT Patent Application No. WO91/00281, published Jan. 10, 1991;
11. Finkelstein, et al., European Patent Application No. EP403159, published Dec. 19, 1990;
12. Chakravarty, et al., European Patent Application No. EP400835, published Dec. 5, 1990;
13. Chakravarty, et al., European Patent Application No. EP400974, published Dec. 5, 1990;
14. Chakravarty, et al., European Patent Application No. EP401030, published Dec. 5, 1990;
15. Roberts, et al., European Patent Application No. EP399731, published Nov. 28, 1990;
16. Roberts, et al., European Patent Application No. EP399732, published Nov. 28, 1990;
17. Narr, et al., European Patent Application No. EP392317, published Oct. 17, 1990; and
18. Kohei, et al., U.S. Pat. No. 4,340598, issued July 20, 1982, which is hereby incorporated by reference.

Other angiotensin II antagonists and methods for their preparation are disclosed in U.S. patent application Ser. No. 580,400, filed Sept. 10, 1990, which is hereby incorporated by reference. The compounds disclosed are compounds of the formula (I):

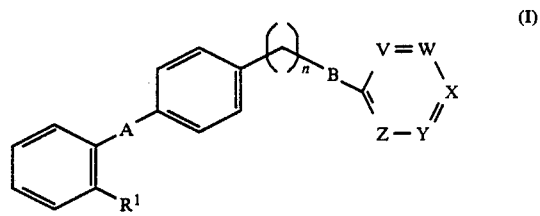

wherein n is 0 or 1;

A is selected from a covalent bond, —O— and —C(O)—;

B is selected from —N($R^4$)—, —O— and —S— wherein $R^4$ is hydrogen, lower alkyl or loweralkoxy-substituted lower alkyl;

$R^1$ is selected from tetrazolyl, —COO$R^5$ and —NHS(O)$_2R^6$, wherein $R^5$ is hydrogen or a carboxy-protecting group and $R^6$ is selected from the lower alkyl and halo-substituted lower alkyl;

V, W, X, Y and Z are independently selected from N, CH, C$R^2$ and C$R^3$, with the proviso that (1) not more than one of V, W, X, Y and Z is C$R^2$, (2) one of V, W, X, Y and Z is C$R^3$, and (3) not more than three of V, W, X, Y and Z are N;

$R^2$ is selected from lower alkyl, lower alkylthio, loweralkoxy-substituted lower alkyl, loweralkylthio-substituted lower alkyl, arylalkyl and N$R^7R^8$ wherein $R^7$ and $R^8$ are independently selected from hydrogen and lower alkyl, or $R^7$ and $R^8$ taken together with the nitrogen atom to which they are attached form a 5- to 7-membered aliphatic heterocycle;

$R^3$ is selected from —CN; —NO$_2$; —NHS(O)$_2R^9$ wherein $R^9$ is selected from lower alkyl and halo-substituted lower alkyl; —COO$R^{10}$ wherein $R^{10}$ is hydrogen or a carboxy-protecting group; —C(O)N$R^{11}R^{12}$ wherein $R^{11}$ and $R^{12}$ are independently selected from hydrogen, lower alkyl, hydroxy-substituted lower alkyl, loweralkoxy-substituted lower alkyl and loweralkoxy-substituted loweralkoxy, or $R^{11}$ and $R^{12}$ taken together with the nitrogen atom to which they are attached form a 5- to 7- membered aliphatic heterocycle; —$CH_2OR^{13}$ wherein $R^{13}$ is selected from hydrogen, lower alkyl; —$C(O)R^{14}$ wherein $R^{14}$ is hydrogen, lower alkyl or aryl; and —$CH_2NHR^{15}$ wherein $R^{15}$ is selected from hydrogen, lower alkyl, —$C(O)R^{16}$, —$C(O)NHR^{16}$ and —$S(O)2R^{17}$ wherein $R^{16}$ is selected from hydrogen, lower alkyl and aryl and $R^{17}$ is selected from lower alkyl and halo-substituted lower alkyl; or a pharmaceutically acceptable salt thereof.

In one embodiment represented by formula (I A), V and X are N, W is $CR^2$ and Z is $CR^3$.

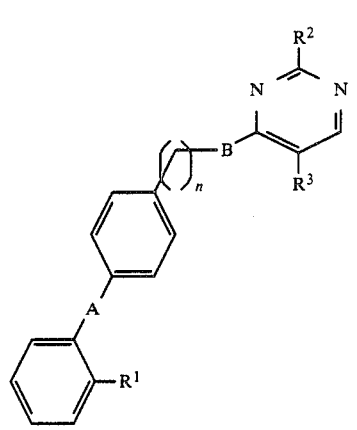
(IA)

In another embodiment represented by formula (I M), V and Z are N, W is $CR^2$ and Y is $CR^3$.

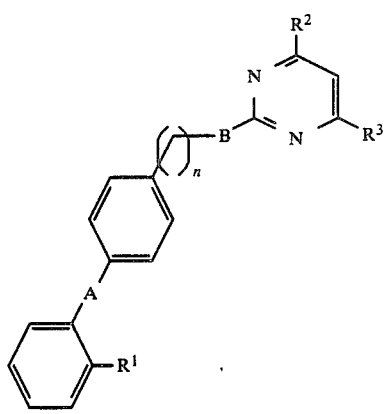
(IM)

In another embodiment represented by formula (IR), X is N, V is $CR^2$ and Z is $CR^3$.

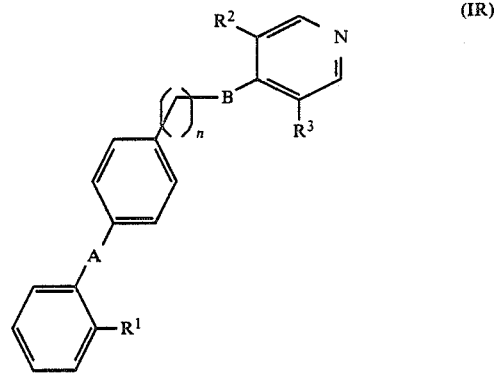
(IR)

In another embodiment represented by formula (I S), W and Z are N, X is $CR^2$ and V is $CR^3$.

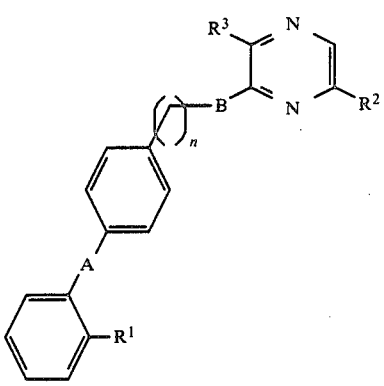
(IS)

In another embodiment represented by formula (I T), V and W are N, and Z is $CR^3$.

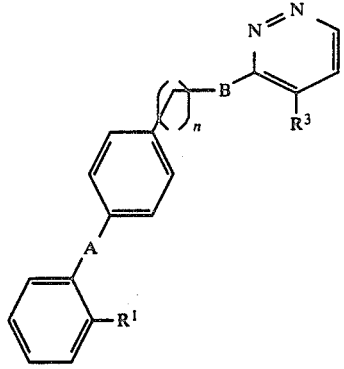
(IT)

In another embodiment represented by formula (I V), Z is N and V is $CR^3$.

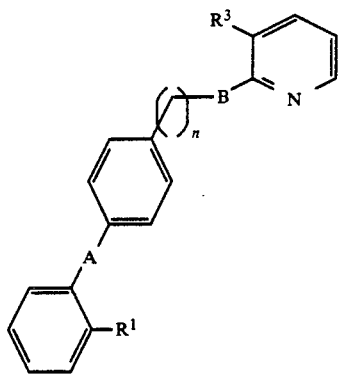

(IV)

In yet another embodiment represented by formula (I W), V is CR³, W, X and Z are N and Y is CR².

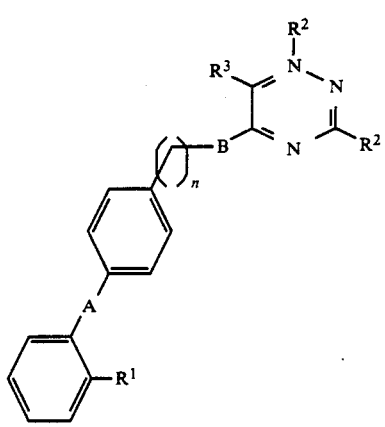

(IW)

The following compounds are representative of the compounds of formula (I):

Ethyl 2-n-butyl-4-[N-{(2'-[1H-tetrazol-5-yl]biphenyl-4-yl)methyl}amino]pyrimidine-5-carboxylate;
2-n-Butyl-5-hydroxymethyl-4-[N-{(2-1H-tetrazol-5-yl)biphenyl-4-yl)methyl}amino]pyrimidine hydrochloride;
Ethyl 2-n-propyl-4-[N-{(2'-[1H-tetrazol-5-yl]biphenyl-4-yl)methyl}amino]pyrimidine-5-carboxylate;
Ethyl 2-n-pentyl-4-[N-{(2'-[1H-tetrazol-5-yl]biphenyl-4-yl)methyl}amino]pyrimidine-5-carboxylate;
Ethyl 2-(1-methylbutyl)-4-[N-{(2'-[1H-tetrazol-5-yl]biphenyl-4-yl)methyl}amino]pyrimidine-5-carboxylate;
Ethyl 2-(1,1-dimethylbutyl)-4-[N-{(2'-[1H-tetrazol-5-yl]biphenyl-4-yl)methyl}amino]pyrimidine-5-carboxylate;
Ethyl 2-(3-methylbutyl)-4-[N-{(2'-[1H-tetrazol-5-yl]biphenyl-4-yl)methyl}amino]pyrimidine-5-carboxylate;
Ethyl 2-[2-(4-fluorophenyl)ethyl]-4-[N-{(2'-[1H-tetrazol-5-yl]biphenyl-4-yl)methyl}amino]pyrimidine-5-carboxylate;
Ethyl 2-(2-ethoxyethyl)-4-[N-{(2'-[1H-tetrazol-5-yl]biphenyl-4-yl)methyl}amino]pyrimidine-5-carboxylate;
Ethyl 2-(2-ethylthioethyl)-4-[N-{(2'-[1H-tetrazol-5-yl]biphenyl-4-yl)methyl}amino]pyrimidine-5-carboxylate;
Ethyl 2-n-butyl-4-[N-{(2'-carboxybiphenyl-4-yl)methyl}amino]-pyrimidine-5-carboxylate;
Ethyl 2-n-butyl-4-[N-(2'-[1H-tetrazol-5-yl]biphenyl-4-yl)amino]pyrimidine-5-carboxylate;
Ethyl 2-butyl-4-[N-methyl-N-(2'-[1H-tetrazol-5-yl]biphenyl-4-yl)amino]pyrimidine-5-carboxylate;
2-Butyl-4-[N-{(2'-[1H-tetrazol-5-yl]biphenyl-4-yl)methyl}amino]pyrimidine-5-carbonitrile;
2-Butyl-4-[N-{2'-[1H-tetrazol-5-yl]biphenyl-4-yl)methyl}amino]pyrimidine-5-carboxamide;
2-Butyl-5-methoxymethyl-4-[N-{(2'-[1H-tetrazol-5-yl]biphenyl-4-yl)methyl}amino]pyrimidine;
2-Butyl-4-[N-{(2'-[1H-tetrazol-5-yl]biphenyl-4-yl)methyl}amino]pyrimidine-5-carboxylic acid hydrochloride;
Ethyl 2-butyl-4-[N-methyl-N-{(2'-[1H-tetrazol-5-yl]biphenyl-4-yl)methyl}amino]pyrimidine-5-carboxylate;
Ethyl 2-methyl-4-[N-butyl-N-{(2'-[1H-tetrazol-5-yl]biphenyl-4-yl)methyl}amino]pyrimidine-5-carboxylate;
Ethyl 2-butyl-4-[(2'-[1H-tetrazol-5-yl]biphenyl-4-yl)thio]pyrimidine-5-acetate;
Ethyl 2-butyl-4-[(2'-[1H-tetrazol-5-yl]biphenyl-4-yl)methoxy]pyrimidine-5-carboxylate;
Ethyl 2-butyl-4-[(2'-[1H-tetrazol-5-yl]biphenyl-4-yl)oxy]pyrimidine-5-carboxylate;
2-Butyl-5-[N-pyrrolidinylcarbonyl]-4-[N-{(2'-[1H-tetrazol-5-yl]biphenyl-4-yl)methyl}amino]pyrimidine;
2-Butyl-5-[N-morpholinocarbonyl]-4-[N-{(2'-[1H-tetrazol-5-yl]biphenyl-4-yl)methyl}amino]pyrimidine;
2-Butyl-5-[N-(4-methoxymethoxy)piperidinocarbonyl]-4-[N-{(2'-[1H-tetrazol-5-yl]biphenyl-4-yl)methyl}amino]pyrimidine;
2-Butyl-5-[N,N-dimethylaminocarbonyl]-4-[N-{(2'-[1H-tetrazol-5-yl]biphenyl-4-yl)methyl}amino]pyrimidine;
2-Butyl-5-[N-methylaminocarbonyl]-4-[N-{(2'-[1H-tetrazol-5-yl]biphenyl-4-yl)methyl}amino]pyrimidine;
2-Butyl-5-[N-(2-hydroxyethyl)aminocarbonyl]-4-[N-{(2'-[1H-tetrazol-5-yl]biphenyl-4-yl)methyl}amino]pyrimidine;
2-Butyl-5-[N-(2-methoxyethyl)aminocarbonyl]-4-[N-{(2'-[1H-tetrazol-5-yl]biphenyl-4-yl)methyl}amino]pyrimidine;
2-Butyl-5-[2-(2'-methoxyethoxy)ethylaminocarbonyl]-4-[N-{(2'-[1H-tetrazol-5-yl]biphenyl-4-yl)methyl}amino]pyrimidine;
2-Butyl-4-[N-{2'-[1H-tetrazol-5-yl]biphenyl-4-yl)methyl}amino]pyrimidine-5-carboxaldehyde;
5-Aminomethyl-2-butyl-4-[N-{(2'-[1H-tetrazol-5-yl]biphenyl-4-yl)methyl}amino]pyrimidine;
2-Butyl-5-[(N-methylamino)carbonylaminomethyl]-4-[N-{(2'-[1H-tetrazol-5-yl]bi-phenyl-4-yl)methyl}amino]pyrimidine;
2-Butyl-5-[N-acetylaminomethyl]-4-[N-{(2'-[1H-tetrazol-5-yl]biphenyl-4-yl)methyl}amino]pyrimidine;
2-Butyl-5-[benzoyloxymethyl]-4-[N-{(2'-[1H-tetrazol-5-yl]biphenyl-4-yl)methyl}amino]pyrimidine;
2-Butyl-5-[methanesulfonamidomethyl]-4-[N-{(2'-[1H-tetrazol-5-yl]biphenyl-4-yl)methyl}amino]pyrimidine;
2-Butyl-5-[1H-tetrazol-5-yl]-4-[N-{(2'-[1H-tetrazol-5-yl]biphenyl-4-yl)methyl}amino]pyrimidine;
Ethyl 2-butyl-4-[N-methyl-N-{(2'-[trifluoromethylsulfonylamido]biphenyl-4-yl)methyl}amino]pyrimidine-5-carboxylate;
Ethyl 2-butyl-4-[N-{4(2'-[1H-tetrazol-5-yl]phenoxy)-phenylmethyl}amino]pyrimidine-5-carboxylate;

Ethyl 2-butyl-4-[N-{4-(2'-[1H-tetrazol-5-yl]benzoyl)-phenylmethyl}amino]pyrimidine-5-carboxylate;

Ethyl 2-butyl-4-[(2'-[1H-tetrazol-5-yl]biphenyl-4-yl)methylthio]pyrimidine-5-carboxylate;

Ethyl 2-propylthio-4-[N-{(2'-[1H-tetrazol-5-yl]biphenyl-4-yl)methyl}amino]pyrimidine-5-carboxylate;

Ethyl-2-(N-piperidino)-4-[N-{(2'-[1H-tetrazol-5-yl]biphenyl-4-yl)methyl}amino]pyrimidine-5-carboxylate;

Methyl 6-n-butyl-2-[N-{(2'-[1H-tetrazol-5-yl]biphenyl-4-yl)methyl}amino]pyrimidine-4-carboxylate;

2-n-Butyl-6-chloro-5-nitro-4-[N-methyl-N-{2'-[1H-tetrazol-5-yl]biphenyl-4-yl)methyl}amino]pyrimidine;

2-n-Butyl-5-amino-4-[N-methyl-N-{(2'-(1H-tetrazol-5-yl]biphenyl-4-yl)methyl}amino]pyrimidine;

2-n-Butyl-5-(methanesulfonylamido)-4-[N-methyl-N-{(2-[1H-tetrazol-5-yl]bi-phenyl-4-yl)methyl}amino]pyrimidine;

Ethyl 5-n-butyl-4-[N-{(2'-[1H-tetrazol-5-yl]biphenyl-4-yl)methyl}amino]pyridine-3-carboxylate;

Methyl 2-[N-butyl-N-{(2'-[1H-tetrazol-5-yl]biphenyl-4-yl)methyl}amino]pyridine-3-carboxylate;

Ethyl 3-[N-{(2'-[1H-tetrazol-5-yl]biphenyl-4-yl)methyl}{amino]pyridazine-4-carboxylate;

Methyl 5-n-butyl-3-[N-{(2'-[1H-tetrazol-5-yl]biphenyl-4-yl)methyl}amino]pyrazine-2-carboxylate;

Ethyl 3-butyl-5-[N-{(2'-[1H-tetrazol-5-yl]biphenyl-4-yl)methyl}amino]-1,2,4-triazine-6-carboxylate; and 2-Methyl-4-{N-butyl-N-[{2'-(1H-tetrazol-5-yl)biphenyl-4-yl}methyl]amino}pyrimidine-5-carboxylic acid hydrochloride The term "aliphatic heterocycle" as used herein refers to a saturated cyclic group containing 5 to 7 ring atoms and, in particular, at least 1 nitrogen atom in the ring and optionally 1 heteroatom selected from S, O and N with the remaining ring atoms being carbon atoms. The ring may be substituted on a carbon atom or a heteroatom, for example with a loweralkoxy or loweralkoxy-substituted loweralkoxy group. Representative aliphatic heterocycles include, pyrrolidine, piperidine, piperazine, morpholine, thiomorpholine and 4-methoxymethoxypiperidine.

The term "aryl" as used herein refers to aromatic radicals having six carbon atoms in a single ring system. Further, the single ring system may be substituted to form a multiple fused ring system. Representative examples of aryl groups include phenyl, 1-naphthyl, 2-naphthyl, and the like. Aryl groups may be substituted with one or more substituents for example, hydroxy, amino, lower alkylamino, halo, lower alkyl, halo-substituted lower alkyl or lower alkoxy.

The term "arylalkyl" is used herein to mean a straight or branched chain radical of one to six carbon atoms which is substituted with an aryl group as defined above. Representative arylalkyl groups include benzyl, phenylethyl groups, fluorobenzyl and fluorphenylethyl.

As used herein, the term "carboxy-protecting group" refers to a carboxy group which has been esterified with one of the commonly used carboxylic acid protecting ester groups employed to block or protect the carboxylic acid functionality while the reactions involving other functional sites of the compound are carried out. In addition, a carboxy-protecting group can be used as a prodrug whereby the carboxy-protecting group can be readily cleaved in vivo, for example by enzymatic hydrolysis, to release the biologically active parent. T. Higuchi and V. Stella provide a thorough discussion of the prodrug concept in "Pro-drugs as Novel Delivery Systems", Vol 14 of the A.C.S. Symposium Series, American Chemical Society (1975). Such carboxy-protecting groups are well known to those skilled in the art, having been extensively used in the protection of carboxyl groups in the penicillin and cephalosporin fields, as described in U.S. Pat. Nos. 3,840,556 and 3,719,667, the disclosures of which are incorporated herein by reference. Examples of esters useful as prodrugs for compounds containing carboxyl groups can be found on pages 14–21 of "Bioreversible Carriers in Drug Design: Theory and Application", edited by E.B. Roche, Pergamon Press:New York (1987). Representative protecting groups include $C_1$ to $C_8$ alkyl (e.g., methyl, ethyl, tertiary butyl), benzyl and substituted derivatives thereof such as alkoxy and nitrobenzyl groups, dialkylaminoalkyl (e.g. dimethylaminoethyl), acyloxyalkyl groups such as pivaloyloxymethyl and propionyloxymethyl.

The term "halo-substituted lower alkyl" refers to a lower alkyl group, as defined below, bearing at least one halogen substituent, for example chloromethyl, fluoroethyl and trifluoromethyl.

The term "lower alkoxy" refers to a lower alkyl group, as defined below, which is bonded through an oxygen atom. Representative examples of lower alkoxy groups include methoxy, ethoxy, t-butoxy and the like.

The term "lower alkyl" refers to branched or straight chain alkyl groups comprising one to six carbon atoms, including, methyl, ethyl, propyl, isopropyl, n-butyl, t-butyl, neopentyl, and the like.

The term "(loweralkyl)amino" refers to amino groups substituted with one or two lower alkyl groups, as defined above, including methylamino, ethylamino, dimethylamino, propylamino and ethylmethylamino.

As used herein the term "loweralkylthio-substituted lower alkyl" refers to a lower alkyl group as defined above attached to a second lower alkyl group through a sulfur atom. Representative loweralkylthio groups include methylthio methyl, methylthioethyl, ethylthioethyl, propylthiomethyl and the like.

The term "phenyl" refers to an unsubstituted benzene radical or a benzene radical substituted with from one to three substituents, for example, halogen, hydroxy, lower alkyl, lower alkoxy or halo-substituted lower alkyl.

The following examples will further serve to illustrate the preparation of the angiotensin II antagonists of the invention.

EXAMPLE 1

Ethyl 2-methyl-4-{N-butyl-N-]2'-(1H-tetrazol-5-yl)biphenyl-4-yl}methyl]amino}pyrimidine-5-carboxylate

EXAMPLE 1A

N-Triphenylmethyl-5-(4'-butylaminomethylbiphenyl-2-yl)tetrazole

N-Triphenylmethyl-5-[2-(4'-bromomethylbiphenyl)]tetrazole (6.00 g, 10.7 mmoles), prepared as described by P. E. Aldrich, et al., European Patent Application No. EP291,969, published Nov. 23, 1988, was dissolved in 55 ml of tetrahydrofuran (THF). Butylamine (40 ml) was added and the mixture was kept at room temperature for 2 hours. The solution was concentrated under vacuum and the resulting residue was dissolved in chloroform. The chloroform solution was washed with dilute aqueous KOH, dried over potassium carbonate and concentrated to provide the desired product, which was taken on directly to the next step.

EXAMPLE 1B

Ethyl 2-methyl-4-{N-butyl-N-[{2'-(N-triphenylmethyltetrazol-5-yl)biphenyl-4-yl}methyl]amino}pyrimidine-5-carboxylate The product of Example 1A was dissolved in 15 ml of THF containing 4.6 ml of triethylamine. A solution of 1.94 g (9.7 mmoles) of ethyl-2-methyl-4-chloropyrimidine-5-carboxylate (E. Peters, et al., J. Org. Chem. 25 2137 (1960)) in 2 ml of THF was added and the resulting solution was stirred at room temperature for 2 hours. The solution was then concentrated and the resulting residue was dissolved in toluene. The toluene solution was extracted with potassium bicarbonate, dried over sodium sulfate and concentrated. The crude product was chromatographed on silica gel eluting with 12% ethyl acetate/88%toluene to provide 4.97 g of the desired product, which was crystallized from ether/hexane (1:1). M.p. 130°–132° C.

EXAMPLE 1C

Ethyl 2-methyl-4-{N-butyl-N-[{2'-(1H-tetrazol-5-yl)biphenyl-4-yl}methyl]amino}pyrimidine-5-carboxylate The product of example 1B (3.5 g, 4.91 mmoles) was suspended in 50 ml of ethanol. Concentrated hydrochloric acid (2.1 ml) was added and the mixture was stirred for 1½ hours at room temperature. The solution was concentrated under vacuum and the resulting residue was diluted with water. Potassium acetate was added in portions until the pH was neutral. Ether (5 ml) was added and the mixture was stirred. The sticky solid which formed was dissolved in chloroform. The chloroform solution was dried over sodium sulfate and then concentrated. The resulting residue was crystallized from ether to provide 2.08 g of the desired product. M.p. 164°–166° C. $^1$H NMR (CDCl$_3$) δ0.85 (t, 3H, J=7 Hz), 1.25 (m, 2H), 1.32 (t, 3H, J=7 Hz), 1.50 (m, 2H), 2.24 (s, 3H), 3.38 (t, 2H, J=7 Hz), 4.30 (q, 2H, J=7 Hz), 4.73 (s, 2H), 7.00 (m, 4H), 7.42 (dd, 1H, J=8 Hz, J=1Hz), 7.50–7.62 (m, 2H), 7.75 (dd, 1H, J=8 Hz, J=1Hz), 8.02 (s, 1H).

EXAMPLE 2

2-Methyl-4-{N-butyl-N-[{2'-(1H-tetrazol-5-yl)biphenyl-4-yl}methyl]amino}pyrimidine--5-carboxylic acid hydrochloride The product of Example 1B (0.6 g, 0.842 mmole) was dissolved in 4 ml of methanol and 6 ml of THF. A solution of 180 mg of lithium hydroxide monohydrate in 1.5 ml of water was added and the mixture was refluxed for 5 hours. After cooling, 1 ml of concentrated hydrochloric acid was added and the mixture was stirred at room temperature for 2 hours. The resulting solution was concentrated under vacuum and 2 ml of water and 3 ml of ether was added to the residue. An oil which was insoluble in both layers formed. The oil was separated and crystallized from acetonitrile to provide 0.289 g of the desired product. M.p. 155°–158° C. $^1$H NMR (CD$_3$OD) δ0.95 (t, 3H, J=7 Hz), 1.30 (m, 2H), 1.69 (m, 2H), 2.60 (s, 3H), 3.70 (m, 2H), 5.08 (m, 2H), 7.10 (d, 2H), 7.20 (s, 2H), 7.55 (d, 2H), 7.5–7.7 (m, 4H), 8.55 (s, 1H).

The ability of a compound to bind to angiotensin II receptors can be demonstrated according to the method of Fluharty, et al., J. Neurochem. 52 1393 (1989).

The ability of a compound which binds to angiotensin II receptors to act as an angiotensin II antagonist can be demonstrated according to the method of Chiu, et al., Hypertension 13 489 (1989).

The ability of an angiotensin II antagonist to treat psoriasis can be demonstrated using the methods outlined in Hofbauer, et al., Br. J. Dermatol. 118 85 (1988); Lowe, et al., Arch. Dermatol. 117 394 (1981); and Du Vivier, et al., J. Invest. Dermatol. 65 235 (1975).

The compounds of the present invention can be used in the form of salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfate, glucoheptonate, glycerophosphate, hemisulfate, heptonate, hexanoate, fumarate, hydrochloride, hydrobromide, hyroiodide, 2-hydroxy-ethansulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate and undecanoate.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metal or alkaline earth metals, such as sodium, potassium, calcium or magnesium or with organic bases.

The novel method of this invention is directed to the use of an angiotensin II antagonist for treating psoriasis in a human or other mammal. This invention is also directed to angiotensin II antagonist compositions useful for treating psoriasis.

Total daily dose administered to a host in single or divided doses may be in amounts, for example, from 0.001 to 50 mg/kg body weight daily and more usually 0.1 to 15 mg/kg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the disease being treated.

The compounds of the present invention may be administered orally, parenterally, by inhalation spray, by nasal spray, rectally or topically in dosage unit formulations containing conventional non-toxic pharmaceutically acceptable carriers, adjuvants and vehicles as desired.

Topical compositions comprising the angiotensin II antagonist can be in the form of shampoos, salves, powders, sprays, ointments, lotions, creams, solutions, suspensions and the like. These topical compositions can be prepared by mixing the angiotensin II antagonist with non-toxic, inert solid or liquid carriers which are suitable for topical administration. Topical administration may also involve the use of transdermal patches or iontophoresis devices.

The term parenteral as used herein includes subcutaneous injections, intravenous, intramuscular, intrasternal injection or infusion techniques. Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, dextrose solution, mannitol solution, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols which are solid at ordinary temperatures, but liquid at the rectal temperature and will therefore melt in the rectum and release the drug.

Solid dosage forms for oral administration may include capsules, tablets, pills, powders and granules, In such solid dosage forms, the active compound may be admixed with at least one inert diluent such as sucrose, lactose or starch. Such dosage forms may also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration may include pharmaceutically acceptable emulsions, solutions, suspensions, syrups and elixirs containing inert duluents commonly used in the art, such as water. Such compositions may also comprise adjuvants, such as wetting agents, emlusifying and suspending agents and sweetening, flavoring and perfuming agents.

In addition to being used as the sole active ingredient for treating psoriasis, an angiotensin II antagonist can be administered in combination with one or more other agents known to be useful for treating psoriasis. Such other agents include anthralin (dihydroxyanthralin), azarabine, colchicine, fluorouracil, methotrexate, methoxsalen (8-methoxypsoralen), resorcinol, retinoids (for example, retinoic acid), corticosteroids (for example, clobetasol propionate, triamcinolone acetonide and the like), cyclosporin, lipoxygenase inhibitors, cyclooxygenase inhibitors, leukotriene synthesis inhibitors, iodochlorhydroxyquin, salicylic acid, vitamin D, dapsone, somatostatin, sulfur, tars, zinc oxide and ultra-violet light treatment. The angiotensin II antagonist and the other agent for treating psoriasis can be administered as part of the same composition or as separate compositions.

The foregoing is merely illustrative of the invention and is not intended to limit the invention to the disclosed compounds and compositions. Variations and changes which are obvious to one skilled in the art are intended to be within the scope and nature of the invention which are defined in the appended claims.

What is claimed is:

1. A method for treating psoriasis comprising administering to a human in need of such treatment a therapeutically effective amount of an angiotensin II antagonist.

2. The method of claim 1 wherein the angiotensin II antagonist is a compound of the formula:

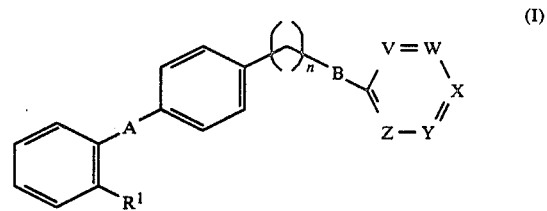

wherein
n is 0 or 1;
A is selected from a covalent bond, —O— and —C(O)—;
B is selected from —N($R^4$)—, —O— and —S— wherein $R^4$ is hydrogen, lower alkyl or loweralkoxy-substituted lower alkyl;
$R^1$ is selected from tetrazolyl, —COO$R^5$ and —NH-S(O)$_2R^6$, wherein $R^5$ is hydrogen or a carboxy-protecting group and $R^6$ is selected from lower alkyl and halo-substituted lower alkyl;
V, W, X, Y and Z are independently selected from N, CH, C$R^2$ and C$R^3$, with the proviso that
(1) not more than one of V, W, X, Y and Z is C$R^2$,
(2) one of V, W, X, Y and Z is C$R^3$, and
(3) not more than three of V, W, X, Y and Z are N;
$R^2$ is selected from lower alkyl, lower alkylthio, loweralkoxy-substituted lower alkyl, loweralkylthio-substituted lower alkyl, arylalkyl and N$R^7R^8$ wherein $R^7$ and $R^8$ are independently selected from hydrogen and lower alkyl, or $R^7$ and $R^8$ taken together with the nitrogen atom to which they are attached form a 5- to 7- membered aliphatic heterocycle;
$R^3$ is selected from —CN; —NO$_2$; —NHS(O)$_2R^9$ wherein $R^9$ is selected from lower alkyl and halo-substituted lower alkyl; —COO$R^{10}$ wherein $R^{10}$ is hydrogen or a carboxy-protecting group; —C(O)N$R^{11}R^{12}$ wherein $R^{11}$ and $R^{12}$ are independently selected from hydrogen, lower alkyl, hydroxy-substituted lower alkyl, loweralkoxy-substituted lower alkyl and loweralkoxy-substituted loweralkoxy, or $R^{11}$ and $R^{12}$ taken together with the nitrogen atom to which they are attached form a 5- to 7- membered aliphatic heterocycle; —CH$_2$O$R^{13}$ wherein $R^{13}$ is selected from hydrogen, lower alkyl; —C(O)$R^{14}$ wherein $R^{14}$ is hydrogen, lower alkyl or aryl; and —CH$_2$NH$R^{15}$ wherein $R^{15}$ is selected from hydrogen, lower alkyl, —C(O)$R^{16}$, —C(O)NH$R^{16}$ and —S(O)2$R^{17}$ wherein $R^{16}$ is selected from hydrogen, lower alkyl and aryl and $R^{17}$ is selected from lower alkyl and halo-substituted lower alkyl; or a pharmaceutically acceptable salt thereof.

3. The method of claim 1 wherein the angiotensin II antagonist is Ethyl 2-methyl-4-{N-butyl-N-({2'-(1H-tetrazol-5-yl)biphenyl-4-yl}methyl)amino}pyrimidine-5-carboxylate.

4. The method of claim 1 wherein the angiotensin II antagonist is 2-Methyl-4-{N-butyl—N-(}2'-(1H-tetrazol-5-yl)biphenyl-4-yl}methyl)amino}pyrimidine-5-carboxylic acid hydrochloride.

5. The method of claim 1 wherein the angiotensin II antagonist is administered topically.

* * * * *